United States Patent
Miltenyi et al.

(10) Patent No.: US 11,633,584 B2
(45) Date of Patent: Apr. 25, 2023

(54) STERILE CONNECTOR (71) Applicant: Miltenyi Biotec GmbH, Bergisch Gladbach (DE)

(72) Inventors: Stefan Miltenyi, Bergisch Gladbach (DE); Winfried Schimmelpfennig, Teterow (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 1267 days.

(21) Appl. No.: 16/123,068

(22) Filed: Sep. 6, 2018

(65) Prior Publication Data
US 2019/0083772 A1 Mar. 21, 2019

(30) Foreign Application Priority Data
Sep. 20, 2017 (EP) .................................... 17192004

(51) Int. Cl.
| A61M 39/18 | (2006.01) |
| A61M 39/14 | (2006.01) |
| B01L 3/00 | (2006.01) |
| A61M 39/10 | (2006.01) |

(52) U.S. Cl.
CPC ............ *A61M 39/18* (2013.01); *A61M 39/14* (2013.01); *B01L 3/563* (2013.01); *A61M 2039/1027* (2013.01); *F16L 2201/44* (2013.01)

(58) Field of Classification Search
CPC .. A61M 39/14; A61M 39/146; A61M 39/165; A61M 39/18; A61M 39/22; A61M 2039/1027; A61M 39/16; A61M 2039/1066; B01L 3/563; B01L 2300/044; B01L 2300/0803; F16L 37/26; F16L 37/1225; F16L 2201/44
USPC .......................................................... 600/133
See application file for complete search history.

(56) References Cited

U.S. PATENT DOCUMENTS

| 243,822 A | * | 7/1881 | Westinghouse, Jr. ... F16L 37/26 285/70 |
| 3,232,578 A | * | 2/1966 | Cousins ................. A61C 17/13 433/95 |
| 3,865,411 A | | 2/1975 | Rowe |
| 4,432,755 A | * | 2/1984 | Pearson ................ A61J 1/2089 604/905 |
| 4,850,350 A | * | 7/1989 | Jackson .............. A61M 1/7413 604/35 |
| 5,810,398 A | * | 9/1998 | Matkovich ............ A61M 39/18 604/209 |
| 5,894,011 A | * | 4/1999 | Prosl ..................... A61M 39/18 210/636 |

(Continued)

Primary Examiner — Kevin F Murphy
Assistant Examiner — Jonathan J Waddy
(74) Attorney, Agent, or Firm — Jaquelin Spong (57) ABSTRACT The invention is directed to an connector comprising a first part and a second part, each provided with a contact surface and at least one non-contact surface facing away from the contact surface, at least one opening in the contact surface having an fluid connection to at least one opening of the non-contact surface, a releasable covering of the opening in the contact surface, and complementary means for mechanically coupling the parts at the contact surfaces to form the connector. The complementary means for mechanically coupling the parts are configured to mechanically interlock with each other.

11 Claims, 6 Drawing Sheets (56) References Cited

U.S. PATENT DOCUMENTS

| | | | | |
|---|---|---|---|---|
| 5,947,954 | A * | 9/1999 | Bonaldo | A61M 39/26 604/905 |
| 6,655,655 | B1 * | 12/2003 | Matkovich | A61M 39/1011 604/905 |
| 2008/0265561 | A1 * | 10/2008 | Buchanan | B29C 66/857 604/28 |
| 2009/0232586 | A1 * | 9/2009 | Diodati | A61M 39/18 403/14 |
| 2010/0230961 | A1 * | 9/2010 | Johnson | F16L 37/0985 285/352 |
| 2013/0184688 | A1 * | 7/2013 | Gagliardoni | A61M 39/1011 29/428 |
| 2013/0289517 | A1 * | 10/2013 | Williams | A61M 39/18 604/500 |
| 2015/0028586 | A1 * | 1/2015 | Gerst | F16L 37/113 285/352 |
| 2016/0053927 | A1 * | 2/2016 | Whitaker | A61M 39/18 137/15.09 |
| 2016/0305574 | A1 * | 10/2016 | Burdge | A61M 39/26 |
| 2017/0284584 | A1 * | 10/2017 | Kesselaar | A61M 39/18 |

\* cited by examiner

STERILE CONNECTOR

CROSS REFERENCE TO RELATED APPLICATIONS

This application is a claims priority to European Application Serial No. 17192004.4, filed Sep. 20, 2017, which is incorporated by reference for all purposes.

STATEMENT REGARDING FEDERALLY SPONSORED RESEARCH

Not applicable.

STATEMENT REGARDING MICROFICHE APPENDIX

Not applicable.

BACKGROUND

The present invention is directed to a connector for sterile connection of tubing sets.

In some technical fields like medicine or biology, it is often required to transfer fluids from one container or device to another under sterile conditions, i.e. at best in absence of any contamination by pollutants, dust, bacteria, viruses, or spores or the like. Unavoidable, connections between the containers have to be provided which may jeopardize sterility.

Devices for sterile connection of tubes, containers or bags in an unsterile environment are known in many variants as "sterile connectors" or simply "connectors". Sterile connectors are known in various modifications, but the most safe connectors in view of sterility usually comprise at least two parts, each connected to a container, which are then mechanically interlocked to provide a fluid connection between the containers. Particular useful to maintain sterility of the devices are connector parts, each provided with an adhesive film protecting the sterile side of the device, which are then removed simultaneously to give way for the fluids.

Examples for such connectors are disclosed in U.S. Pat. Nos. 9,295,825 and 3,865,411. Both publications describe sterile connectors wherein two parts are mechanically combined and a releasable film is removed from both parts at once, the connection is made. By simultaneously removing the releasable films, a sterile passage between the parts i.e. through the connector is provided.

Maintaining sterility is especially difficult in connecting freezing bags, which are commonly used for long-term storage of sterile samples at deep temperatures as for example provided by liquid nitrogen. Besides that all materials used for deep temperature storage need to be certified for stability, the connector still needs to provide a water- and gas tight connection in presence of condensing moisture, ice and unsterile air. A further cause of sterility loss is mishandling the connector, for example by incomplete mechanical connection of the connector parts, premature removing one or both releasable films or not simultaneous removing the releasable films.

Object of the invention was to provide a connector with build-in features to maintain sterility and to avoid mishandling and/or unintentionally abolishing sterility, especially under deep temperature storage conditions.

SUMMARY

Accordingly, the invention is directed to a Connector comprising a first part and a second part, each provided with a contact surface and at least one non-contact surface facing away from the contact surface
- at least one opening in the contact surface having an fluid connection to at least one opening of the non-contact surface
- a releasable covering of the opening in the contact surface complementary means for mechanically coupling the parts at the contact surfaces to form the connector
- characterized in that the complementary means for mechanically coupling the parts are configured to mechanically interlock with each other by counter-rotating of the first and second part; and
- the openings in the contact surfaces are configured to be brought to match at least in part to provide fluid communication through the openings by counter-rotating of the first and second part.

Furthermore, the invention is directed to a tubing set comprising at least one tube, at least one freeze bag and at least one connector of the invention. The freeze bag of such tubing set may comprise at least one recess to accommodate least one connector. This variant greatly simplifies the storage of the freeze bag in a low-temperature environment without struggling with the tubing.

The connector according to the invention is configured to allow fluid communication only when sterility of the fluids is ensured. To this end, the connector is provided with mechanical safety features and releasable coverings of the opening. Further, the connector can be stored with the freezing bag in a flat manner since the openings of the connector for attaching the tubing set are optionally positioned orthogonal to each other.

BRIEF DESCRIPTION OF THE DRAWINGS

In the figures discussed below, similar reference numbers are intended to refer to similar structures, and the structures are illustrated at various levels of detail to give a clear view of the important features of this novel device. It should be understood that these drawings do not necessarily depict the structures to scale, and that directional designations such as "top," "bottom," "upper," "lower," "left" and "right" are arbitrary, as the device may be constructed and operated in any particular orientation.

It should be understood that the drawings are not necessarily to scale, and that like numbers maybe may refer to like features.

DETAILED DESCRIPTION

The present invention is directed to a connector for tubing sets, especially for freezing bags which enables a safe and sterile connection of at least two tubes in an unsterile environment. A preferred application of the connector is to connect a sterile sample in a freezing bag to a sterile tubing set in an unsterile environment.

The connector comprises a first and a second part, each provided with complementary means for mechanically coupling of the parts at the contact surfaces by counter-rotating of the parts. The term "counter-rotating of the parts" shall mean that the parts are brought in contact with the respective contact surfaces and then are rotated in opposite directions around a common rotational axis and includes the rotation of one part against the other part in an idle (non-rotational) state. For this propose, the connector is provided with complementary means for mechanically coupling 11, 21, which interact by counter rotation of the parts like a bayonet coupling. Further, appropriate means for mechanically interlocking the parts in the final position may be provided, for example flap (13a) shown in FIG. 3 locks into opening or recess 23a in counterpart 23.

The first and second part of the connector are optionally provided with means to optically indicate the relative position of the first and second part to each other during counter-rotating of the parts. Such means can be markings on the parts, for example printed signs or any three-dimensional object/form extending from the parts which can be "felt" when counter rotating the parts during the closing process. For example, objects 13 and 23 shown in the figures may serve as such markings.

Figure 1:
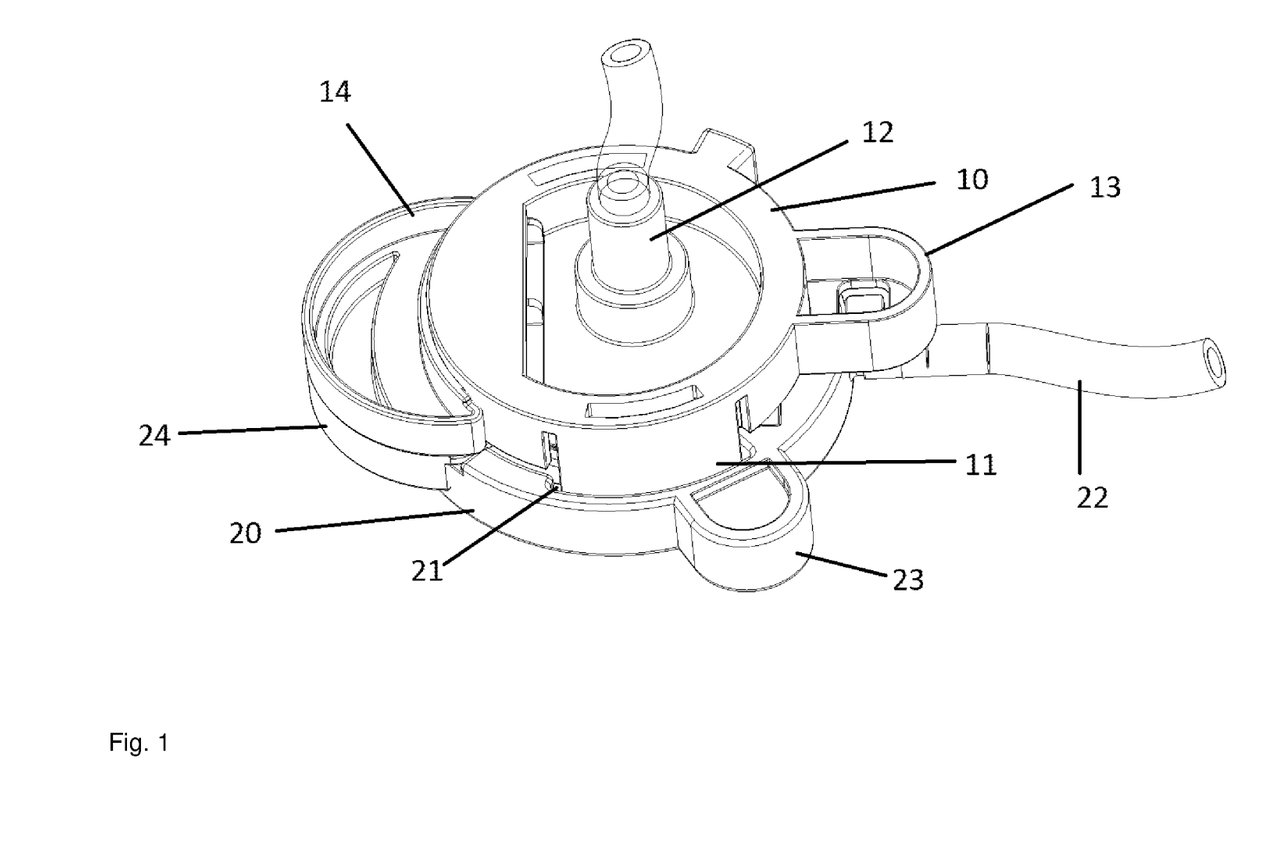
FIG. 1 shows an assembled connector of the invention with upper and lower part 10 and 20, complementary means for mechanically coupling 11 and 21, openings in the non-contact surfaces 12 and 22, means for mechanically interlocking 13 and 23, grips for releasable covering 14 and 24.
Figure 2:
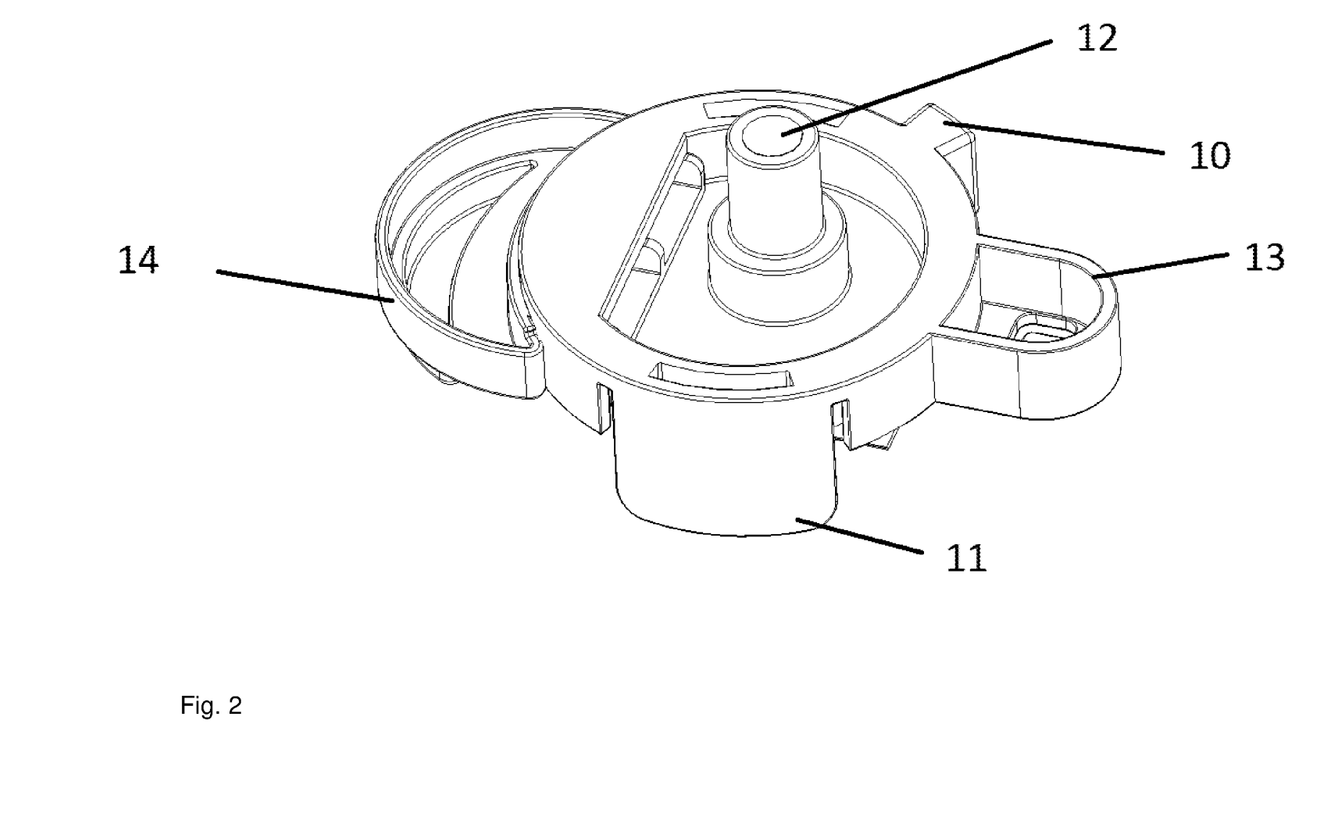
FIG. 2 shows one (upper) part (10) of the connector in top view with complementary means for mechanically coupling 11, opening in the non-contact surface 12, means for mechanically interlocking 13, grip for releasable covering 14.
Figure 3:
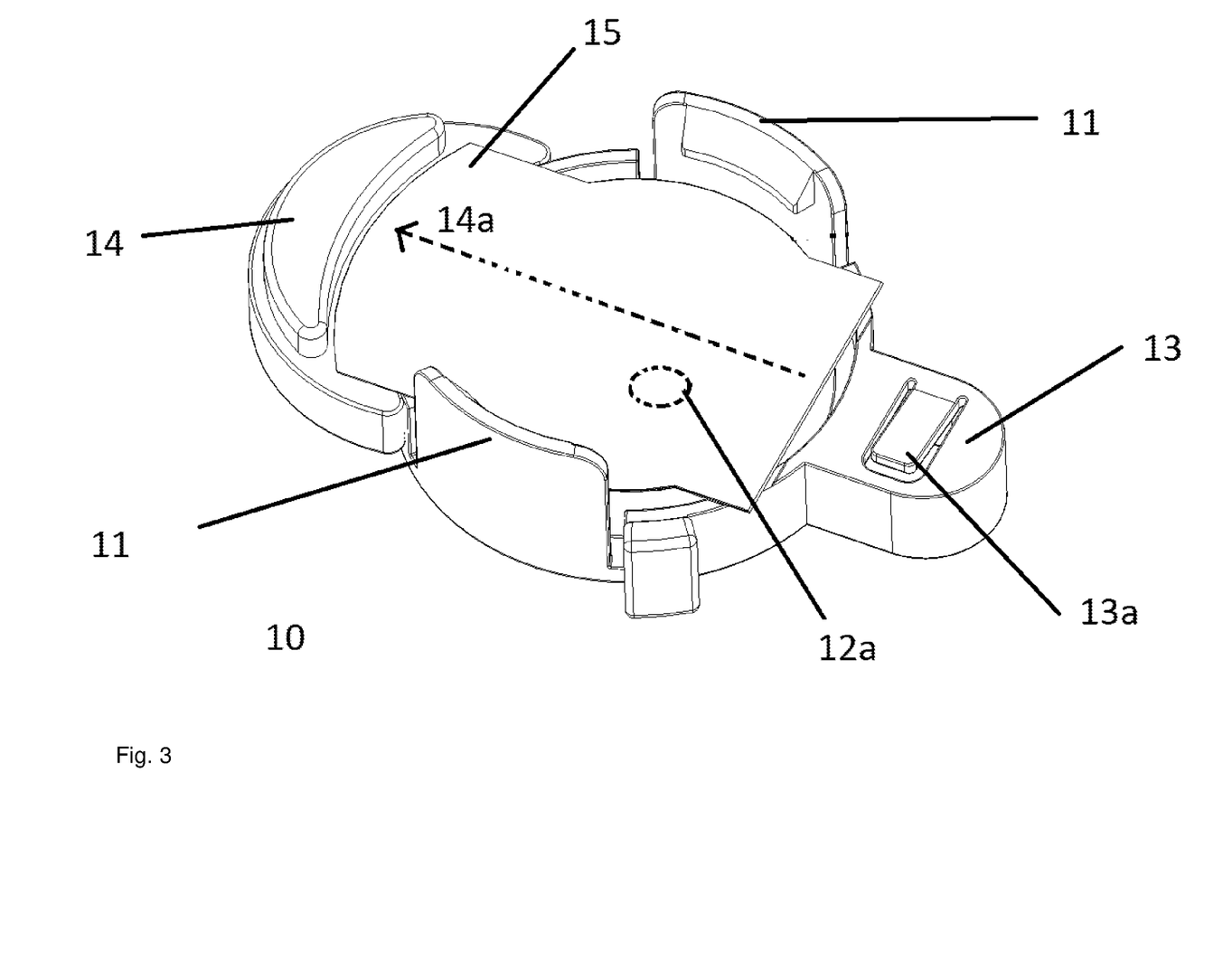
FIG. 3 shows one (upper) part (10) of the connector in bottom view with complementary means for mechanically coupling 11, opening in the contact surface 12a, means for mechanically interlocking 13, grip for releasable covering 14, releasable covering 15.
Figure 4:
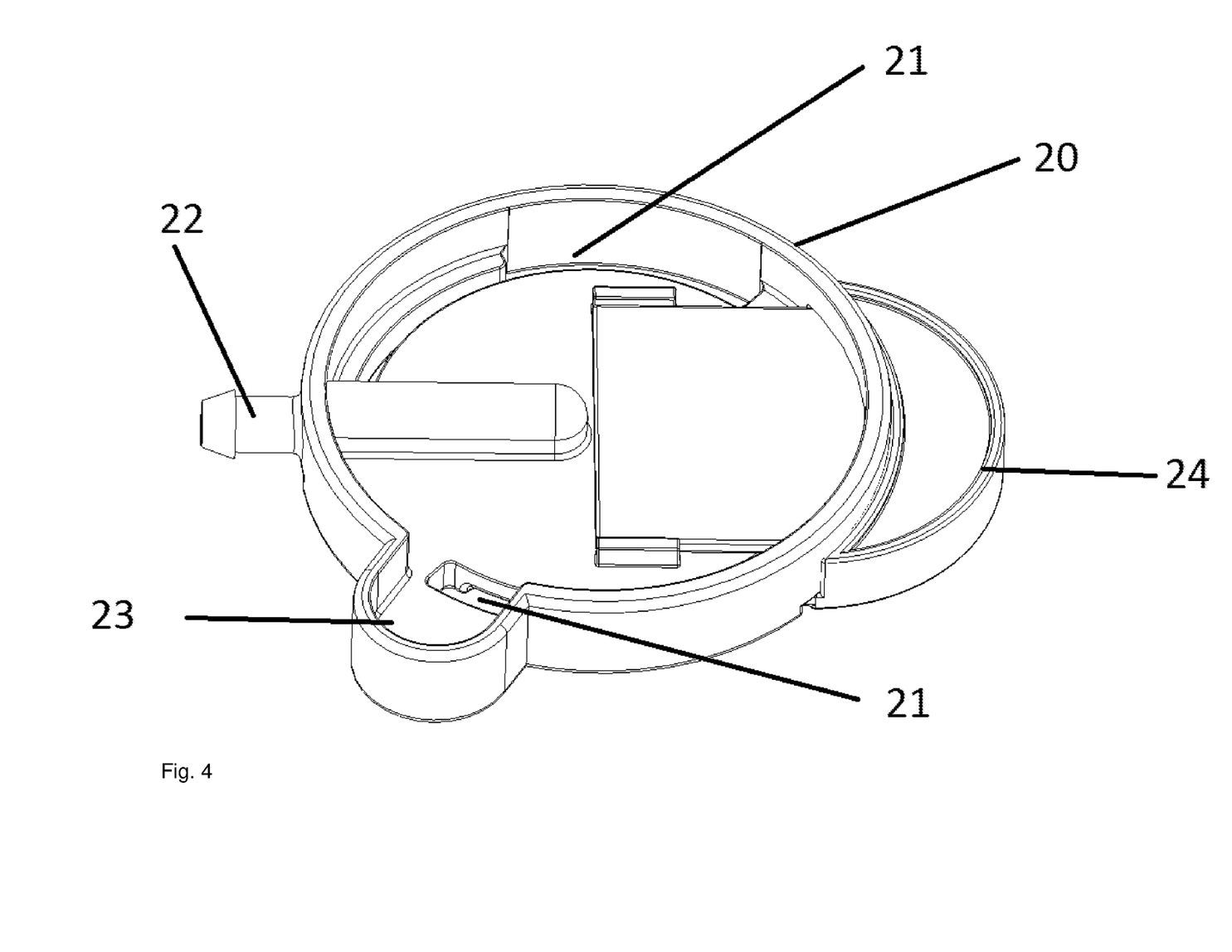
FIG. 4 shows one (lower) part (20) of the connector in top view complementary means for mechanically coupling 21, openings in the non-contact surface 22, means for mechanically interlocking 23, grip for releasable covering 24.
Figure 5:
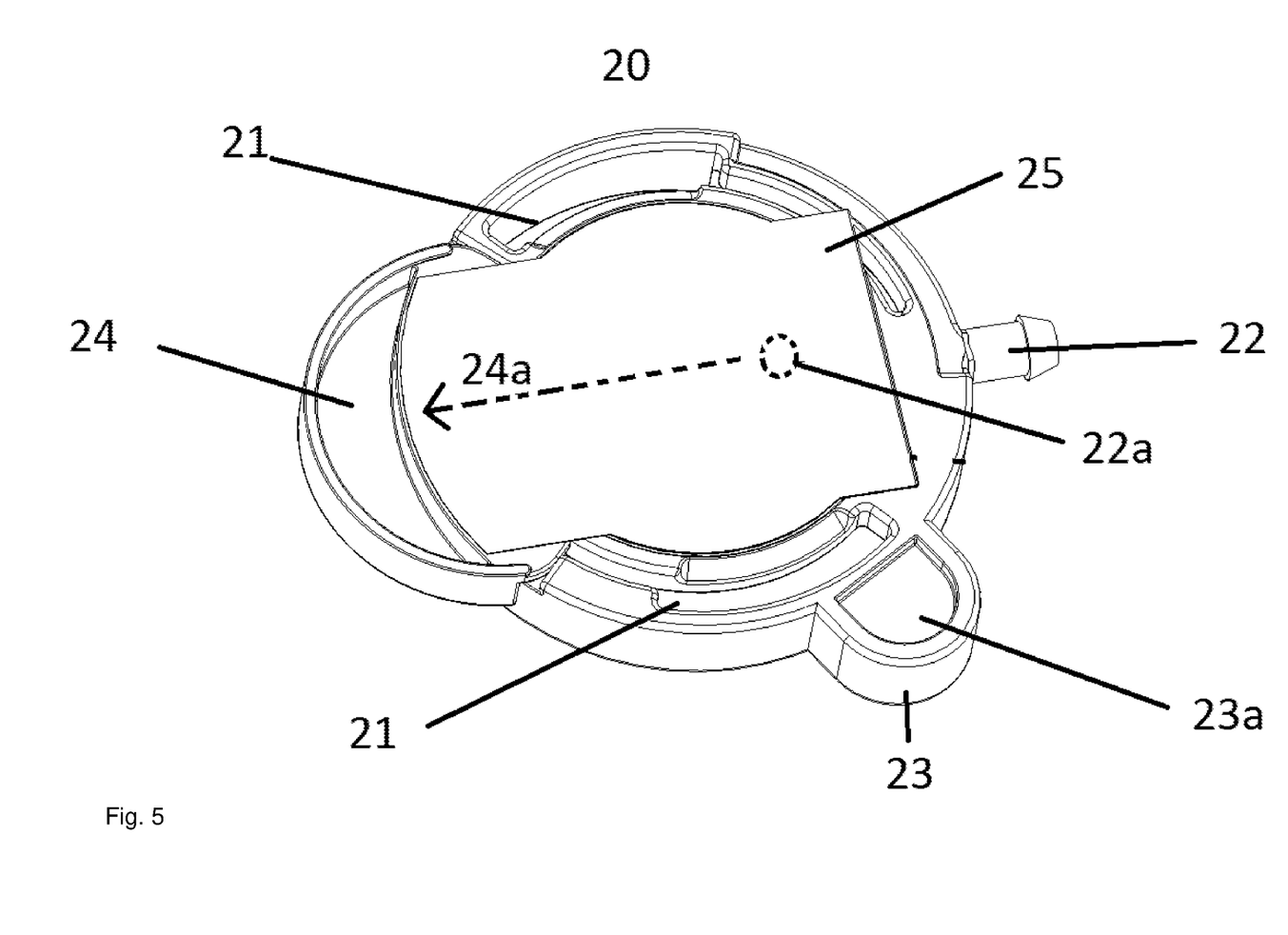
FIG. 5 shows one (lower) part (20) of the connector in bottom view with complementary means for mechanically coupling 21, openings in the contact surface 22a, means for mechanically interlocking 23, grip for releasable covering 24, releasable covering 25.
Figure 6:
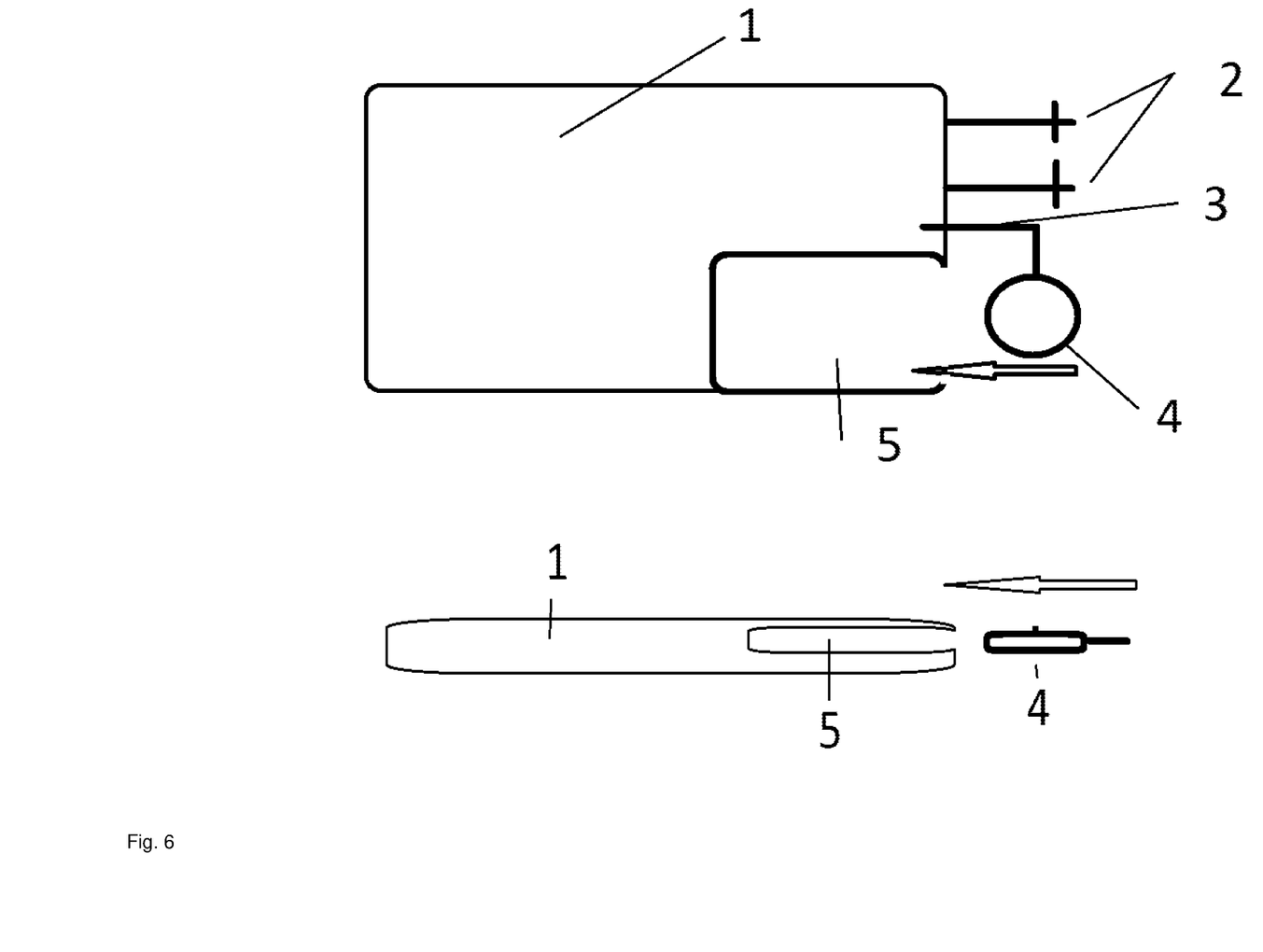
FIG. 6 shows the connector (4) with the freezing bag (1) having a recess (5) in top and side view. Usually freezing bags (1) have i/o ports for filling purposes (2). Tube (3) is in fluidic communication to sterile connector (4) which can be inserted into recess (5) for storage purposes.

In another embodiment, the openings of the first and second parts are located not in the rotational axis of first and second part which is defined by the centre of the counter-rotation of the first and second part during coupling. In other words, the openings in the contact surfaces of the first part and second part can only brought to match and provide fluid communication through the openings when the parts are rotated into the final, locked position. FIGS. 3 and 5 indicate the "asymmetric" position of the openings 12a and 22a.

Preferable, at least one of the openings of the first and second parts is provided with a gasket.

If the connector shall be fixed during operation at a stand or the like, it is preferred that the openings in the non-contact surfaces of at least one connector part are orthogonal to each other. In this variant (as shown in the drawings), one opening is located "on top" of one part and the other opening at a side of the other part of the connector. In other variants, both openings are located "on top" or at the side of both parts of the connector.

In order to connect the connector with tubes, the openings in the non-contact surfaces should be provided with an appropriate connecting adapter, especially with a Luer-lock adapter.

In another embodiment, the first part and second part are provided with means that prevent the openings in the contact surfaces of the first part and second part to be brought to match before the release coverings are removed from the openings and the parts are rotated to the locked position. This is shown in the figures, where the grips 14 and 24 are configured as recesses which interlock before both grips (and the release coverings) can be removed from the connector. Accordingly, grips 14 and 24 provide the means for preventing the releasable covering from being removed before the first and second ports are coupled.

The connector according to the invention is provided with releasable coverings for the openings in the contact surfaces. The releasable coverings ensure that the openings and/or the contact surfaces are sterile up to the moment when the connector is used i.e. the releasable coverings are removed. The releasable coverings are preferable made from soft polymeric films like PE or PS or siliconized paper as known in the art and are glued or welded on the contact surfaces.

The connector/the parts of the connector is sterilized by processes known to a person skilled in the art, like autoclaving, irradiating or chemical treatment.

In a preferred variant of the invention, the releasable coverings of the openings in the contact surface are attached to extricable grips. "Attached" means that the releasable coverings are glued or mechanically bound to the extricable grips in a way that by extracting the grips from the parts of the connector, the releasable coverings are removed from the openings.

FIGS. 3 and 5 show the releasable coverings 15 and 25 attached to grips 14 and 24 in the respective parts of the connector. Grips 14 and 24 can be extracted from the parts in the direction as indicated by dotted lines 14a and 15a.

In order to prevent undesired loss of sterility by removing the releasable coverings subsequently and not simultaneously, the grips of the releasable coverings of the first part and second part are provided with complementary means for mechanically interlock with each other. This locking additional prevents an early counter-rotating of the first and second part.

Preferable, the first part and the second part is provided with means to prevent the release coverings from being removed from the openings before the first part and second part are mechanically coupled.

In a preferred embodiment, the releasable coverings are adhered as a folded double layer to the contact surfaces configured to be peeled off the openings by simultaneously removing the mechanically interlocked grips at least in part from the mechanically interlocked first part and second part.

The releasable coverings may be glued or welded to the contact surfaces.

In a further embodiment to ensure that sterility is maintained, the releasable coverings are simultaneously removed from the openings of the first part and second part by simultaneously removing the mechanically interlocked grips at least in part from the mechanically interlocked first part and second part.

In a further embodiment, the extricable grips are provided with a blocking means that prevents further counter-rotating of the first and second part until both grips are extracted from the interlocked parts. By extracting the grips, the blocking means is removed and further counter-rotating of the first and second part into the final position is possible. Optionally the openings of the parts are brought to match at least in part to provide fluid communication when the parts are rotated to the final position.

Process of Manufacture of the Device

The device of the invention may be manufactured by any method known to a person skilled in the art. Preferred methods are injection molding and 3D printing, for example by extrusion deposition, fused deposition modeling, stereolithography or photopolymer digital light processing.

In a preferred variant, one part of the connector (like the first part) is fixed to the freezing bag and the respective other part (like the second part) is fixed to a tubing set.

The connector should be manufactured from materials certified for medical use and certified for stability at deep temperatures like −190° C. Examples for such materials are EVA and PE-UHMW or LCP (Ethylene Vinyl Acetat, Poly Ethylene Ultra High Molecular Weight, Liquid Crystal Polymere)).

To assemble the connector, first the grip 14 or 24 are positioned with part 10 or 20 and the releasable covering 15 or 25, then the coverings are welded or glued onto the contact surfaces. The parts are now ready for sterilization.

Use of the Device

The device of the invention is configured to connect two tubes i.e. to provide fluid communication between two tubes in a sterile manner and therefore is provided with the above described safety means.

The handling sequence of the coupling process may further be described as follows:

1. Provide the two parts of the connector as described and place adjacent to each other with the respective contact surfaces.

2. Slide-in the clips of the first into the matching gaps of the second part, thereby mechanically interlocking the parts and additional interlocking the extricable grips.

3. Simultaneously remove the interlocked grips at least in part from the mechanically interlocked first part and second part and simultaneously removing the a releasable covering of the openings and removing the blocking means 4. Further counter-rotate the first and second part into the final position thereby bringing the openings of the parts to match at least in part to provide fluid communication between the openings and connected tubing set.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. For example, while the disclosure describes a number of fabrication steps and exemplary dimensions for the device, it should be understood that these details are exemplary only, and that the systems and methods disclosed here may be applied to any number of alternative designs. Accordingly, the exemplary implementations set forth above, are intended to be illustrative, not limiting.

What is claimed is:

1. A medical device with a connector comprising:
    a first part and a second part, each provided with
        a contact surface and at least one non-contact surface facing away from the contact surface,
        at least one opening in the contact surface having a fluid connection to at least one opening of the non-contact surface,
        a releasable covering of the opening in the contact surface, and
        complementary means for mechanically coupling the parts at the contact surfaces to form the connector; and
    a medical tubing set, comprising at least one freeze bag and at least one tube, wherein the at least one freeze bag is coupled to the connector and the at least one tube, wherein the freeze bag comprises at least one recess into which the connector is inserted, with the freeze bag and connector in fluid communication within the recess; and
    characterized in that the complementary means for mechanically coupling the parts are configured to mechanically interlock with each other by counter-rotation of both the first and second parts about a single rotational axis which is orthogonal to the contact surfaces; and the openings in the contact surfaces are configured to be brought to match at least in part to provide fluid communication through the openings by counter-rotation of both the first and second parts about the rotational axis, wherein the openings in the contact surfaces of the first and second parts are not located in the rotational axis of the first and second parts which is defined by the centre of the counter-rotation of the first and second parts during coupling.

2. The connector according to claim 1, characterized in that the releasable coverings of the openings in the contact surfaces are attached to extricable grips.

3. The connector according to claim 2, characterized in that the extricable grips are provided with complementary means for mechanically interlocking with each other.

4. The connector according to claim 2, characterized in that the first part and the second part are provided with grips which interlock before both grips and the release coverings can be removed together from the connector.

5. The connector according to claim 1, characterized in that the releasable coverings are adhered as a folded double layer to the contact surfaces and configured to be peeled off the openings in the contact surfaces by simultaneously removing the mechanically interlocked grips at least in part from the mechanically interlocked first part and second part.

6. The connector according to claim 1, characterized in that the releasable coverings are welded to the contact surfaces.

7. The connector according to claim 1, characterized in that the first part and second part are provided with means that prevent the openings in the contact surfaces of the first part and second part to be brought to match at least in part to provide fluid communication through the openings before the releasable coverings are removed from the openings and the parts are rotated to the locked position.

8. The connector according to claim 1, characterized in that the first and second parts are provided with means to optically indicate the relative positions of the first and second parts to each other during counter-rotation of the parts.

9. The connector according to claim 1, characterized in that at least one of the openings of the first and second parts in the contact surfaces is provided with a gasket.

10. The connector according to claim 1, characterized in that the openings in the non-contact surfaces are orthogonal to each other.

11. The connector according to claim 1, characterized in that the openings in the non-contact surfaces are each provided with a Luer-lock adapter.

* * * * *